United States Patent [19]

Nakamura et al.

[11] Patent Number: 4,982,037
[45] Date of Patent: Jan. 1, 1991

[54] PROCESS FOR SELECTIVELY ALKYLATING BIPHENYL

[75] Inventors: Tadashi Nakamura, Kodaira; Shouichi Hoshi, Iwaki; Yoshio Okada, Matsudo, all of Japan

[73] Assignee: Kureha Kagaku Kogyo Kabushiki Kaisha, Tokyo, Japan

[21] Appl. No.: 426,500

[22] Filed: Oct. 23, 1989

[30] Foreign Application Priority Data

Mar. 13, 1987 [JP] Japan .................................. 62-58348

[51] Int. Cl.$^5$ .............................................. C07C 2/68
[52] U.S. Cl. ..................................... 585/467; 585/446
[58] Field of Search ................................ 585/467, 446

[56] References Cited

U.S. PATENT DOCUMENTS

| | | | |
|---|---|---|---|
| 3,539,622 | 11/1970 | Heck | 585/427 |
| 3,851,004 | 11/1974 | Yang | 585/467 |
| 4,143,084 | 3/1979 | Kaeding et al. | 585/467 |
| 4,365,104 | 12/1982 | Kaeding et al. | 585/467 |
| 4,447,666 | 5/1984 | McWilliams | 585/467 |

FOREIGN PATENT DOCUMENTS

| | | | |
|---|---|---|---|
| 0012514 | 6/1980 | European Pat. Off. | 585/467 |
| 0141514 | 5/1985 | European Pat. Off. | 585/467 |
| 0243554 | 11/1987 | European Pat. Off. | |
| 0244531 | 11/1987 | European Pat. Off. | |
| 2132568 | 9/1973 | Fed. Rep. of Germany | |
| 156222 | 12/1981 | Japan | |
| 8200103 | 1/1982 | PCT Int'l Appl. | |

OTHER PUBLICATIONS

Azerb Khim. Zh(1), 21–26, (1971).
Synthesis, vol. 11, p. 822 (1978).
Patent Abstracts of Japan, vol. 6, No. 7, 1982.

*Primary Examiner*—Chung K. Pak
*Attorney, Agent, or Firm*—John P. White

[57] ABSTRACT

Disclosed herein is a process for selectively synthesizing the para-isomer of alkylbiphenyl in the alkylation of biphenyl with propylene or butene, employing zeolite having a molar ratio of $SiO_2$ to $Al_2O_3$ of not less than 10, as a catalyst.

3 Claims, No Drawings

PROCESS FOR SELECTIVELY ALKYLATING BIPHENYL

This is a continuation of application Ser. No. 160,655, filed Feb. 26, 1988, now abandoned.

BACKGROUND OF THE INVENTION

Many aromatic alkyl compounds are useful in various fields, and those having a substituent at a para-position are especially important.

The present invention relates to a process for producing with good selectivity a compound having an alkyl group at a para-position of biphenyl.

Among the compounds produced by the process according to the present invention, para-isopropylbiphenyl is useful as a solvent for a dye for pressure-sensitive recording paper, and 4,4'-di-isopropylbiphenyl is convertible to 4,4'-biphenyl dicarboxylic acid or 4,4'-dihydroxybiphenyl by oxidation of side chains.

As a process for producing an alkylbiphenyl, (1) a method of reacting biphenyl with an olefin or an alkyl halide in the presence of a Friedel-Crafts catalyst such as aluminum chloride and (2) a method of reacting biphenyl with an olefin or an alcohol by using a solid acid catalyst such as silica alumina and zeolite are known. These methods, however, have a low selectivity for para-isomers.

Japanese Patent Application Laid-Open (KOKAI) No. 56-156,222 (1981) discloses a method of producing an alkylbiphenyl which is rich in meta- and para-isomers by reacting biphenyl with an olefin while applying silica alumina or zeolite as a catalyst. However, the ratio of para-isomer to meta-isomer in the alkylbiphenyl obtained by this method is not always high enough. This reference does not disclose any process for producing a 4,4'-dialkyl compound.

The following methods are known as a process for producing 4,4'-dialkylbiphenyl.

(1) Synthesis, (11) 822, (1978).

A method of reacting the iodonium salt of diaryl with $CH_3MgS$ in the presence of $NiCl_2$ as a catalyst. Since the raw material is difficult to obtain, this method cannot be industrially practicable.

(2) Japanese Patent Publication No. 47-10,705 (1972), U.S. Pat. No. 3,539,622.

A method of producing 4,4'-dialkylbiphenyl from an aromatic mercury compound using $CuCl_2$, $PdCl_2$ or LiCl as a catalyst. This reference also discloses a process for producing p,p,-bicumyl (4,4'-di-isopropylbiphenyl). However, a method using a mercury compound is unfavorable in view of influence on a human body.

(3) Azerb. Khim. Zh (1) 21-6 (1971).

A method of producing dialkylbiphenyl by reacting an aromatic halide with metallic sodium is described. This method, however, includes many side reactions such as dehalogenation etc., and the yield of the aimed product is rather low. The use of metallic sodium cannot be an industrial method.

On the other hand, many patents have been presented mainly by Mobil Oil for a process about selective alkylation of an aromatic group by using zeolite. Many of these patents are directed to producing a p-dialkylbenzene and no process to produce an alkylbiphenyl is found except one disclosed in the above Japanese Patent Application Laid-Open (KOKAI) No. 56-156,222 (1981).

Biphenyl derivatives having a substituent at a para-position includes not only p-phenylphenol, 4,4'-dihydroxybiphenyl, which are already under commercial production, but also many useful derivatives such as p-isopropylbiphenyl, p-isopropenylbiphenyl and 4,4'-biphenyl dicarboxylic acid. However, processes for producing these derivatives have not reached a sufficient level, and development of an economical process has been wanted earnestly.

As a result of the extensive studies performed by the present inventors in view of such situation, the present invention has been achieved.

SUMMARY OF THE INVENTION

The object of the present invention is to provide a process for producing, with good selectivity, a biphenyl derivative having an alkyl group at a para-position.

It is another object of the present invention to provide an alkylation process for selectively obtaining a para-isomer of an alkylbiphenyl from propylene or butene by applying, as a catalyst, zeolite in which the molar ratio of $SiO_2$ to $Al_2O_3$ is not less than 10.

It is still another object of the present invention to provide an alkylation process for selectively obtaining a para-isomer of an alkylbiphenyl by using a Mordenite type zeolite or a ZSM-5 type zeolite as a catalyst.

DETAILED DESCRIPTION OF THE INVENTION

The present invention provides an alkylation process for selectively obtaining a para-isomer of an alkylbiphenyl in the alkylation of biphenyl with propylene or butene, characterized in that a zeolite having $SiO_2/Al_2O_3$ (molar ratio) of not less than 10, preferably 10 to 50 is used as a catalyst. As examples of a preferable zeolite, Mordenite type and ZSM-5 type zeolites can be exemplified. In both cases, those with the ions exchanged with $H^+$ are preferable because of the strong activity, but it is not necessary that the ions are completely exchanged by $H^+$. However, zeolites substituted largely, for instance, by $NH_4^+$ or alkali metals are impractical because of their low activity.

Among silica alumina catalysts other than a zeolite, there are some which have an excellent alkylation activity, but they have a low selectivity for para-isomers. Y-, L- and A-type zeolites, in other words, zeolites having the molar ratio of $SiO_2$ to $Al_2O_3$ is less than 10, do not exhibit good selectivity for para-isomers, either. Since the isomer selectivity of these zeolites is poor, they are unsuitable as a catalyst for achieving the object of the present invention.

The molar ratio of $SiO_2$ to $Al_2O_3$ of the zeolite catalyst for the present invention should not be less than 10, however, when it is too large, the reaction activity itself is apt to become lower, so that the ratio is preferably not to be more than 50.

The preferable molar ratio of an olefin to biphenyl in the raw materials is generally 0.5 to 2.2. The molar ratio is appropriately determined depending upon whether the intended product is a monoalkylated compound, dialkylated compound or both of them. However, when the molar ratio of the olefin to biphenyl is less than 0.5, the amount of unreacted biphenyl becomes impractically large. On the other hand, if the molar ratio is 2.2 or more, an unnecessarily large amount of trialkylated compound is unfavorably produced.

The reaction temperature is 200° to 320° C., preferably 220° to 300° C. The temperature is determined within this range depending on the activity of the catalyst and the degree of reaction (alkylation degree). The alkylation degree is obtained from the following formula, wherein each component of the reaction mixture is expressed by molar fraction:

Alkylation degree = (monoalkylated compound) + [2 × (dialkylated compound)] + [3 × (trialkylated compound)] + [4 × (tetra-alkylated compound)]

When the reaction temperature is lower than 200° C., the reaction rate is impractically low, while the reaction temperature higher than 320° C. unfavorably brings about the production of heavy compound, which lead to deterioration of the catalyst and increases the by-products due to decomposition alkylation reactions.

The para-alkylbiphenyl produced by the process according to the present invention can be separated from other products and purified by conventional distillation and/or crystallization. Other by-products, for example, a meta-alkylbiphenyl is convertible to a para-alkylbiphenyl by a known trans-alkylation method or the like. The para-alkylbiphenyl obtained, which is useful by itself, can be converted to another useful para-substituted bipheny by oxidizing side chains.

EXAMPLE 1

Into an 1 liter autoclave made of stainless steel, 616 g of biphenyl and 30 g of TSZ-640 HOA (Mordenite type zeolite produced by Toyo Soda Co., Ltd., molar ratio of $SiO_2$ to $Al_2O_3$ is 19.0) were charged, and the temperature was raised to about 250° C. Propylene was supplied under stirring while maintaining the pressure at 1 kg/cm²G, thereby bringing the mixture into reaction at 250° C. for 5 hours.

The composition of reaction product and other data are shown in Table 1.

EXAMPLE 2

The reaction was carried out at 250° C. for 3 hours by using TSZ-640 HOA in the same way as in Example 1.
The results are shown in Table 1.

EXAMPLE 3

The reaction was carried out at 270° C. for 15 hours by using TSZ-640 HOA in the same way as in Example 1.
The results are shown in Table 1.

EXAMPLE 4

The reaction was carried out at 200° C. for 5 hours in the same way as in Example 1 except that 60 g of TSZ-640 HOA was used as the catalyst.
The results are shown in Table 1.

EXAMPLE 5

The propylation reaction was carried out at 230° C. for 15 hours in the same way as in Example 1 except that 30 g of TSZ-600 HOA (Mordenite type zeolite produced by Toyo Soda Co., Ltd., molar ratio of $SiO_2$ to $Al_2O_3$ is 10.2) was used as the catalyst.
The results are shown in Table 1.

TABLE 1

| | | | Propylation of Biphenyl in The Presence of Mordenite-type Zeolite as The Catalyst | | | | | | | |
|---|---|---|---|---|---|---|---|---|---|---|
| Example | Catalyst | Reaction Temp. (°C.) | Composition of the Reaction Product (mol %) | | | | | | Propylation degree | Selectivity for p-derivative (%) |
| | | | Biphenyl | MIPB*(1) | p-MIPB*(2) | DIPB*(3) | 4,4'-DIPB*(4) | *(5) | | |
| 1 | *(6) | 250 | 25.0 | 46.3 | 30.4 | 28.1 | 17.1 | 0.6 | 1.04 | 63.3 |
| 2 | *(6) | 250 | 43.5 | 42.1 | 28.8 | 14.2 | 9.2 | 0.2 | 0.71 | 67.3 |
| 3 | *(6) | 270 | 1.1 | 22.4 | 11.3 | 70.3 | 37.2 | 6.2 | 1.82 | 49.0 |
| 4 | *(6) | 200 | 27.6 | 47.4 | 31.8 | 24.4 | 16.2 | 0.6 | 0.98 | 66.3 |
| 5 | *(7) | 230 | 20.4 | 44.8 | 25.7 | 33.3 | 11.3 | 1.5 | 1.15 | 46.5 |

*(1)MIPB means monoisopropylbiphenyl.
*(2)p-MIPB means para-isopropylbiphenyl in MIPB
*(3)DIPB means diisopropylbiphenyl
*(4)4,4'-DIPB means 4,4'-diisopropylbiphenyl in DIPB
*(5) Total mol % of biphenyls substituted with propyl groups of not less than 3.
*(6) TSZ-640HOA is used as the catalyst
*(7) TSZ-600HOA is used as the catalyst The alkyl biphenyls were analyzed by gas chromatography. The operating conditions were as follows:

| Column: | SUS Golay column (0.25 mmΦ × 45 m) |
|---|---|
| Temperature: | 150° C. |
| Carrier gas: | helium |
| Detector: | FID |

The selectivity for the para-isomer was calculated with the following formula by using the analyzed values of the reaction mixture (containing unreacted biphenyl):

$$\text{Para-isomer selectivity}(\%) = \frac{\text{P-MIPB(mol \%)} + 4,4'\text{-DIPB(mol)}}{100 - \text{unreacted biphenyl(mol \%)}} \times 100$$

wherein MIPB represents monoisopropylbiphenyl, and DIPB di-isopropylbiphenyl.

COMPARATIVE EXAMPLE 1; REACTION USING A SILICA ALUMINA CATALYST

The propylation reaction was carried out at 240° C. for 2 hours in the same way as in Example 1 except that 60 g of silica alumina X-630 HN (produced by Nikki Chemical Co., Ltd., containing 27% of $Al_2O_3$) was used as the catalyst.
The results are shown in Table 2.

COMPARATIVE EXAMPLE 2; REACTION USING A Y-TYPE ZEOLITE

The propylation reaction was carried out at 200° C. for 2 hours in the same way as in Example 1 except that 30 g of Y-type zeolite TSZ-330 HUA (produced by Toyo Soda Co., Ltd., molar ratio of $SiO_2$/ to $Al_2O_3$ is 6) was used as the catalyst.

The results are shown in Table 2.

COMPARATIVE EXAMPLE 3; REACTION USING AN L-TYPE ZEOLITE

The propylation reaction was carried out at 200° C. for 1 hour in the same way as in Example 1 except that 30 g of L-type zeolite TSZ-500 HOA (produced by Toyo Soda Co., Ltd., molar ratio of $SiO_2$ to $Al_2O_3$ is 6) was used as the catalyst.

The results are shown in Table 2.

$Al_2O_3$ is 23.3; H type) was used as the catalyst. The composition of the reaction product is as follows:

| Component | Composition (mol %) |
|---|---|
| Biphenyl | 53.7 |
| Monoisopropyl-biphenyl | 31.5 |
| (p-monoisopropyl-biphenyl) | (17.2) |
| Di-isopropyl-biphenyl | 12.8 |
| (4,4'-di-isopropyl biphenyl) | (2.4) |
| Tri- or more isopropyl biphenyl | 2.0 |
| Propylation degree | 0.63 |
| Selectivity for para-isomer | 42.3 |

TABLE 2

Comparative Examples of Propylation of Biphenyl

| Com. Ex. No. | Catalyst | $SiO_2$/$Al_2O_3$ (mol ratio) | Reaction Temp. (°C.) | Composition of the Reaction Product (mol %) | | | | | | Propylation degree | Selectivity for p-derivative (%) |
|---|---|---|---|---|---|---|---|---|---|---|---|
| | | | | Biphenyl | MIPB*(1) | p-MIPB*(2) | DIPB*(3) | 4,4'-DIPB*(4) | *(5) | | |
| 1 | *(6) | 4.5 | 240 | 30.6 | 46.8 | 21.9 | 21.4 | 2.9 | 1.2 | 0.93 | 35.7 |
| 2 | *(7) | 6 | 200 | 6.4 | 34.1 | 15.4 | 50.8 | 5.7 | 8.7 | 1.62 | 22.5 |
| 3 | *(8) | 6 | 200 | 31.1 | 47.1 | 18.0 | 21.4 | 2.0 | 0.4 | 0.91 | 29.0 |

*(1)MIPB means monoisopropylbiphenyl.
*(2)p-MIPB means para-isopropylbiphenyl in MIPB.
*(3)DIPB means diisopropylbiphenyl.
*(4)4,4'-DIPB means 4,4'-diisopropylbiphenyl in DIPB
*(5) Total mol % of biphenyls substituted with propyl groups of not less than 3.
*(6) Silica-Alumina
*(7) Y- type zeolite.
*(8) L- type zeolite.

EXAMPLE 6; BUTYLATION REACTION

Butylation reaction was carried out at 260° C. for 4 hours by using 2-butene in place of propylene and 30 g of TSZ-640 HOA as the catalyst in the same way as in Example 1.

The composition of the reaction product and other data are shown in Table 3.

EXAMPLE 7; BUTYLATION REACTION

The butylation reaction was carried for 6 hours in the same way as in Example 6 except for using 60 g of TSZ-640 HOA.

The composition of the reaction product and other date are shown in Table 3.

What is claimed is:

1. An alkylation process to obtain selectively para-isopropylbiphenyl or 4,4'-diisopropylbiphenyl in an alkylation of biphenyl with propylene comprising the step of using, as a catalyst, a Mordenite zeolite having a molar ratio of $SiO_2$ to $Al_2O_3$ of not less than 10.

TABLE 3

Butylation of Biphenyl in The Presence of Mordenite-Type Zeolite as The Catalyst

| Example No. | Compostion of The Reaction Product (mol %) | | | | | Butylation degree | Selectivity for p-derivative (%) |
|---|---|---|---|---|---|---|---|
| | Biphenyl | MSBB*(1) | p-MSBB*(2) | DSBB*(3) | 4,4'-DSBB*(4) | *(5) | |
| 6 | 49.4 | 41.1 | 34.2 | 9.5 | 7.9 | 0.0 | 0.60 | 83.2 |
| 7 | 23.0 | 51.7 | 39.1 | 24.9 | 18.4 | 0.4 | 1.03 | 74.7 |

*(1)MSBB means mono-sec-butylbiphenyl.
*(2)p-MSBB means para-sec-butylbiphenyl in MSBB.
*(3)DSBB means di-sec-butylbiphenyl.
*(4)4,4'-DSBB means 4,4'-di-sec-butylbiphenyl in DSBB.
*(5) Total mol % of biphenyl substituted with butyl group of not less than 3.

EXAMPLE 8

The propylation reaction of biphenyl was carried out at 260° C. for 2 hours in the same way as in Example 1 except that 30 g of TSZ-821 (ZSM-5 type zeolite produced by Toyo Soda Co., Ltd., molar ratio of $SiO_2$ to 2. The alkylation process according to claim 1, wherein a molar ratio of propylene and biphenyl is 0.5 to 2.2.

3. The alkylation process according to claim 1, wherein the reaction temperature of said alkylation is 200° to 320° C.

* * * * *